(12) United States Patent
Forster et al.

(10) Patent No.: US 9,962,559 B2
(45) Date of Patent: May 8, 2018

(54) MULTI-SEGMENTED INFLATABLE BRACHYTHERAPY DEVICES, SYSTEMS, AND METHODS OF USING THE SAME

(75) Inventors: Kenneth M. Forster, Dallas, TX (US); Matthew C. Biagioli, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days. days.

(21) Appl. No.: 14/005,394

(22) PCT Filed: Mar. 16, 2012

(86) PCT No.: PCT/US2012/029487
§ 371 (c)(1),
(2), (4) Date: Sep. 16, 2013

(87) PCT Pub. No.: WO2012/125946
PCT Pub. Date: Sep. 20, 2012

(65) Prior Publication Data
US 2014/0005539 A1    Jan. 2, 2014

Related U.S. Application Data

(60) Provisional application No. 61/453,405, filed on Mar. 16, 2011.

(51) Int. Cl.
*A61N 5/10* (2006.01)
*A61M 29/02* (2006.01)
(Continued)

(52) U.S. Cl.
CPC ............ *A61N 5/1007* (2013.01); *A61B 5/055* (2013.01); *A61B 5/4836* (2013.01); *A61B 6/032* (2013.01);
(Continued)

(58) Field of Classification Search
CPC .. A61N 5/1007; A61N 5/1039; A61N 5/1016; A61N 5/1014; A61N 5/1002; A61M 31/005; A61M 29/02; A61M 25/1011; A61M 2025/1061; A61M 2025/1054; A61M 2025/1059;
(Continued)

(56) References Cited

U.S. PATENT DOCUMENTS 3,872,856 A  *  3/1975  Clayton ........................... 600/6
4,554,909 A  *  11/1985  Pino y Torres ................ 600/6
(Continued)

FOREIGN PATENT DOCUMENTS

WO      2008008089 A2    1/2008

OTHER PUBLICATIONS

International Preliminary Report on Patentability for International Application No. PCT/US2012/029487, dated Sep. 17, 2013.
(Continued)

*Primary Examiner* — Christine H Matthews
*Assistant Examiner* — Kaylee Wilson
(74) *Attorney, Agent, or Firm* — Meunier Carlin & Curfman LLC

(57) ABSTRACT

Provided are multi-segmented inflatable brachytherapy devices. Also provided are systems and methods including multi-segmented inflatable brachytherapy devices.

25 Claims, 8 Drawing Sheets

(51) Int. Cl.
*A61B 5/055* (2006.01)
*A61B 5/00* (2006.01)
*A61B 6/03* (2006.01)
*A61B 6/00* (2006.01)
*A61M 31/00* (2006.01)
*A61M 25/10* (2013.01)
*A61B 90/00* (2016.01)

(52) U.S. Cl.
CPC ............ *A61B 6/481* (2013.01); *A61M 29/02* (2013.01); *A61M 31/005* (2013.01); *A61N 5/1002* (2013.01); *A61N 5/1014* (2013.01); *A61N 5/1016* (2013.01); *A61N 5/1039* (2013.01); *A61B 2090/0427* (2016.02); *A61B 2090/0436* (2016.02); *A61B 2090/0481* (2016.02); *A61M 25/1011* (2013.01); *A61M 2025/1061* (2013.01)

(58) Field of Classification Search
CPC ... A61M 2025/1011; A61M 2025/1015; A61B 2018/00577; A61B 2019/4081; A61B 2019/4036; A61B 2019/4027; A61B 5/055; A61B 5/4836; A61B 6/481; A61B 6/032
See application file for complete search history.

(56) References Cited

U.S. PATENT DOCUMENTS

| | | | | |
|---|---|---|---|---|
| 5,370,685 | A * | 12/1994 | Stevens | 623/2.11 |
| 5,913,813 | A | 6/1999 | Williams et al. | |
| 6,390,968 | B1 | 5/2002 | Harmon | |
| 2002/0165521 | A1* | 11/2002 | Cioanta | A61B 18/04 604/509 |
| 2009/0299327 | A1* | 12/2009 | Tilson | A61B 17/8816 604/500 |
| 2010/0036190 | A1 | 2/2010 | Murphy et al. | |
| 2010/0168665 | A1 | 7/2010 | Skerven | |
| 2010/0234668 | A1* | 9/2010 | Roeder et al. | 600/3 |
| 2010/0331601 | A1* | 12/2010 | Partridge | A61N 5/1015 600/6 |
| 2012/0215053 | A1* | 8/2012 | Gim | 600/6 |

OTHER PUBLICATIONS

International Search Report and Written Opinion for International Application No. PCT/US2012/029487, dated Oct. 31, 2012.
Saini, et al., "Dose Reductions Study in Vaginal Balloon Packing Filled With Contrast For HDR Brachytherapy Treatment," Int. J. Radiation Oncology Biol. Phys., 2010, pp. 1-5.

* cited by examiner

MULTI-SEGMENTED INFLATABLE BRACHYTHERAPY DEVICES, SYSTEMS, AND METHODS OF USING THE SAME

CROSS REFERENCE TO RELATED APPLICATIONS

This application claims the benefit of U.S. Provisional Application No. 61/453,405, filed on Mar. 16, 2011, and is a 371 National phase of PCT US2012/029487, filed Mar. 16, 2012, both of which are incorporated by reference herein in their entirety.

TECHNICAL FIELD

The present application relates to multi-segmented inflatable brachytherapy devices and includes systems and methods that incorporate multi-segmented inflatable brachytherapy devices.

BACKGROUND

Brachytherapy procedures for the treatment of cancer use radioactive sources placed in or close to tumors. There has been a rebirth of this treatment technique with the advent of high dose-rate computer controlled brachytherapy. This technique can deliver very high doses in a short period of time. The source is driven to the tumor through a catheter or through a series of catheters. The radiation from the source can damage tissue, but has a very sharp fall off as you move away from the source.

SUMMARY

Provided are multi-segmented inflatable brachytherapy devices. Also provided are systems and methods that incorporate multi-segmented inflatable brachytherapy devices. For example, provided are sleeves comprising multiple inflatable segments for positioning on a brachytherapy applicator. The multi-segmented inflatable sleeves are optionally used to move tissue away from a radiation source during brachytherapy treatment.

An example sleeve for positioning on a brachytherapy applicator includes a first inflatable segment and a second inflatable segment, both of which have primary lumens. The first and second segments are selectively inflatable by delivery of fluid into each lumen. Optionally, the sleeve has a central passage configured for positioning over the brachytherapy applicator.

The brachytherapy applicator optionally comprises a distal ring. The sleeve optionally has a proximal end and a distal end. The distal end is optionally configured for positioning proximal to the distal ring of the brachytherapy applicator. The sleeve optionally has at least one conduit. The conduit is optionally configured for delivering fluid into the primary lumen of the first segment. Furthermore, one or more conduit is optionally configured for delivering fluid into the primary lumen of the second segment.

The first inflatable segment may further comprise a second lumen located at least partially within the primary lumen of the first segment. The first inflatable segment may optionally have at least one conduit in fluid communication with the second lumen. The second lumen is optionally configured to accept fluid delivered through the at least one conduit.

The second inflatable segment may further comprise a second lumen located at least partially within the primary lumen of the second segment. The second inflatable segment may optionally have at least one conduit in fluid communication with the second lumen. The second lumen is optionally configured to accept fluid delivered through the at least one conduit.

Each inflatable segment optionally comprises two or more lumens. The fluid accepted into one or more lumen is optionally a contrast agent. At least one conduit for removal of fluid from the primary or second lumen of the first segment is optionally provided. The volume of fluid administered into the second lumen of the first segment optionally corresponds to the volume of fluid removed from the primary lumen of the second segment. The volume of fluid administered into the second lumen of the second segment optionally corresponds to the volume of fluid removed from the primary lumen of the second segment.

The first segment is optionally configured to assume an inflated shape from fluid delivered into the primary lumen of the first segment. For example, the inflated shape is substantially maintained upon administration of fluid to the second lumen of the first segment and removal of the corresponding fluid volume from the primary lumen of the first segment.

The second segment is optionally configured to assume an inflated shape from fluid delivered into the primary lumen of the second segment. For example, the inflated shape is substantially maintained upon administration of fluid to the second lumen of the second segment and removal of the corresponding fluid volume from the primary lumen of the second segment.

Optionally, a securing member for securing the sleeve to the brachytherapy applicator is provided. The sleeve optionally comprises at least one additional inflatable segment having a primary lumen. For example, the at least one additional inflatable segment is selectively inflatable by delivery of fluid into the lumen. The at least one additional inflatable segment optionally comprises a second lumen disposed at least partially within the first lumen of the additional segment. Optionally, each inflatable segment is configured to assume an inflated shape from fluid delivered into the primary lumen of each respective segment.

An example system for providing brachytherapy treatment includes a brachytherapy applicator for insertion into a cavity of a subject. The system further includes a sleeve for positioning about the brachytherapy applicator. The sleeve includes a first inflatable segment having a primary lumen and a second inflatable segment having a primary lumen. The first and second segments are selectively inflatable by selective delivery of fluid into each primary lumen. The system further includes a fluid delivery apparatus for delivering fluid into each primary lumen. The fluid delivery system delivers the fluid with sufficient force to cause inflation of each segment and movement of subject tissue when the applicator and sleeve are positioned within a cavity. For example, the cavity is optionally selected from the group consisting of vagina, anus, rectum, esophagus, gastro-intestinal track, and a vessel.

An example method for treating a cancerous, precancerous, or proliferative condition includes positioning a brachytherapy applicator into a cavity of a subject. The method further includes positioning a sleeve about the applicator. The sleeve has a first inflatable segment with a primary lumen, as well as a second inflatable segment with a primary lumen. The first and second segments are selectively inflatable by delivery of fluid into each lumen. After positioning the sleeve about the brachytherapy applicator and positioning the applicator into the cavity of a subject, at least one inflatable segment is inflated by administering fluid into the primary lumen of each inflatable segment to move tissue of the subject away from the brachytherapy applicator. For example, the fluid administered is water.

Optionally, an image is taken of the subject to visualize a treatment field of the subject. Each inflatable segment optionally includes a second lumen. For example, the second lumen is optionally located at least partially within the primary lumen of each respective inflatable segment contrast agent solution is optionally administered to each second lumen while allowing a volume of water corresponding to the volume of administered contrast agent solution to be removed from each primary lumen.

Radiation may optionally be applied to a subject. During the application of radiation, the inflatable segments may optionally reduce radiation delivered to the tissue of the subject moved away from the brachytherapy applicator. Optionally, the cavity is selected from the group consisting of vagina, anus, rectum, esophagus, gastro-intestinal track, and a vessel. For example, the cavity is a vagina and the sleeve is optionally positioned proximate to the cervix.

An example method for reducing radiation exposure of tissue in a subject includes inflating an inflatable device with a contrast agent. By inflating the inflatable device, the size of the device expands and causes movement of tissue. The method further includes applying radiation to the subject, wherein exposure of the moved tissue is reduced.

These and other features and advantages of the present invention will become more readily apparent to those skilled in the art upon consideration of the following detailed description and accompanying drawings, which describe both the preferred and alternative embodiments of the present invention.

DETAILED DESCRIPTION

Figure 1A:
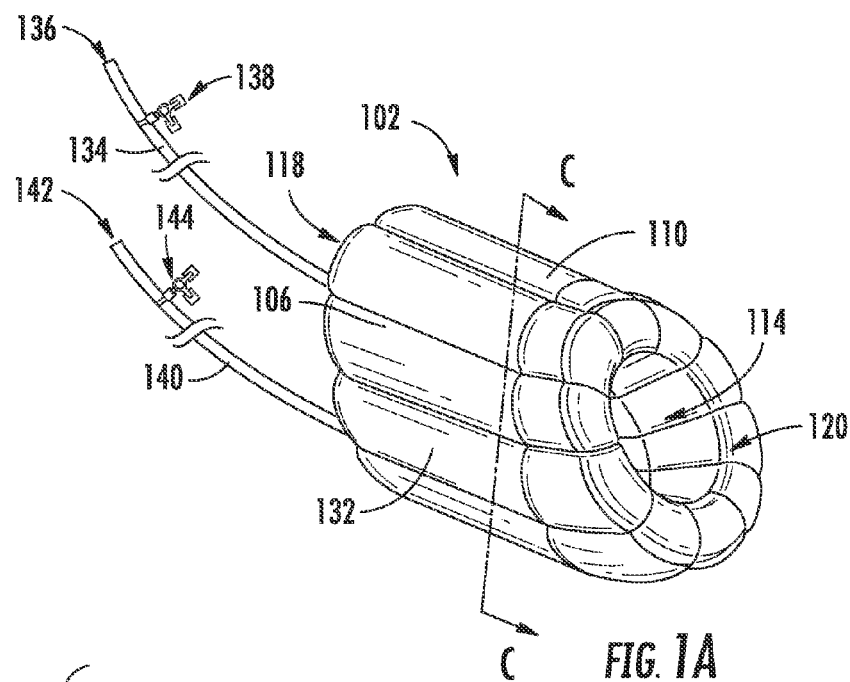
FIG. 1A is a schematic illustration of an example multi-segmented inflatable sleeve for use in brachytherapy treatment.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

As used in the specification, and in the appended claims, the singular forms "a," "an," "the," include plural referents unless the context clearly dictates otherwise.

The term "comprising" and variations thereof as used herein are used synonymously with the term "including" and variations thereof and are open, non-limiting terms.

The present application relates to multi-segmented inflatable brachytherapy devices including systems and methods that incorporate multi-segmented inflatable brachytherapy devices. For example, provided are sleeves for positioning on a brachytherapy applicator, also referred to herein as an applicator. Optionally, the brachytherapy applicator is configured for insertion within a cavity of a subject.

Brachytherapy procedures for the treatment of cancer use radioactive sources placed in or close to tumors. There has been a rebirth of this treatment technique with the advent of high dose-rate computer controlled brachytherapy. This technique can deliver very high doses in a short period of time. The source is driven to the tumor through a catheter or through a series of catheters. The radiation from this source has a very sharp fall off as you move away from the source. Owing to the proximity of the radiation source, brachytherapy offers the advantage of delivering a more localized dose to the target tissue region. In order to minimize side effects of the radiation, the catheters are attached to an interstitial applicator and the treatment is repeated up to 10 times in separate sessions.

Brachytherapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and permanent or temporary brachytherapy.

Brachytherapy can be performed by implanting radiation sources directly into the tissue to be treated. Interstitial brachytherapy is traditionally carried out using radioactive seeds such as $I^{125}$ seeds. These seeds, however, produce inhomogeneous dose distributions. In order to achieve a minimum prescribed dosage throughout a target region of tissue, a large number of seeds are used, resulting in very high doses being delivered to tissue in proximity to the seed, which can cause radionecrosis in healthy tissue.

In general, the amount of radiation desired by the physician is a certain minimum amount that is delivered to a region up to about two centimeters away from the margin of the excised tumor. It is desirable to keep the radiation that is delivered to the tissue in the target treatment region within a narrow absorbed dose range to prevent over-exposure to tissue at or near the radiation source, while still delivering the minimum prescribed dose at the maximum prescribed distance from the radiation source.

The devices, systems and methods described herein can move tissues away from close proximity to a radiation source. This allows the irradiated tissue to be in a region of shallow dose gradient and results in a reduced risk of hot-spots and radionecrosis.

The devices, systems and methods described in this application relate to multi-segmented inflatable devices whose segments can be inflated with either solution or air. This can allow the physician performing the brachytherapy procedure to move the sources closer to the tumor and further away from the critical normal structures. In addition, the segmented inflatable devices allow for accurate repositioning of the applicator without the need for re-imaging the patient (CT or MRI or both) and re-planning the brachytherapy treatment.

The segmented inflatable device design is used to differentially move normal anatomy further away from brachytherapy applicators to reduce tissue toxicity while at the same time providing a method for repositioning the applicators without the need for re-imaging the patient and re-planning the brachytherapy treatments for patients treated with multifraction brachytherapy.

Figure 1B:
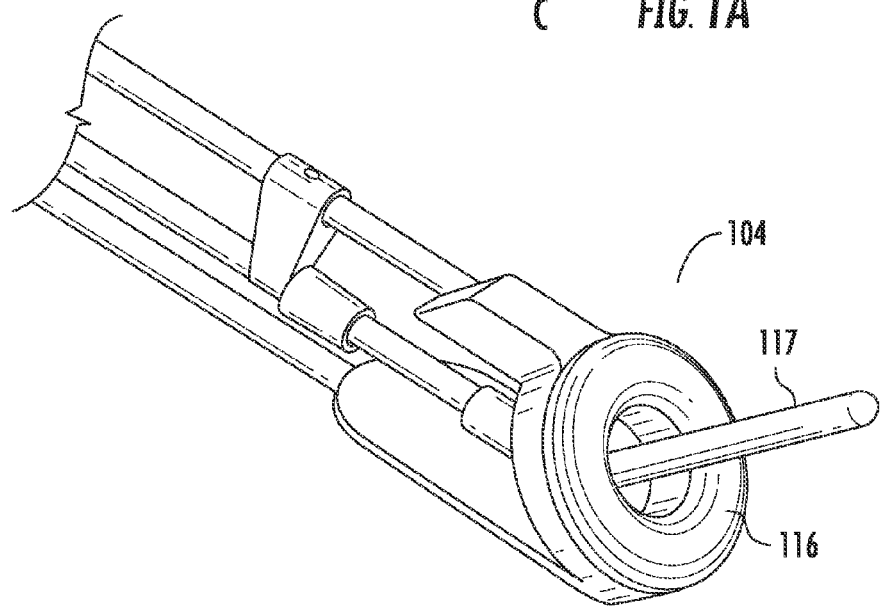
FIG. 1B is a schematic illustration of an example applicator for use in brachytherapy treatment.
Figure 1C:
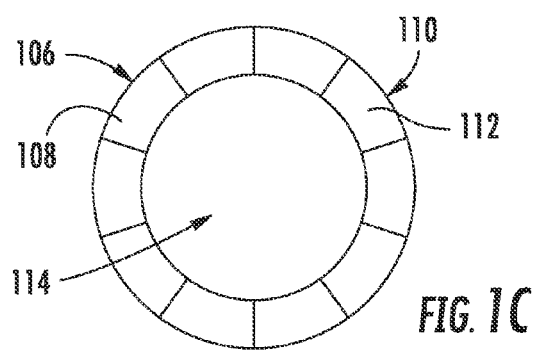
FIG. 1C is a schematic illustration of the cross-section across line C-C of FIG. 1A.
Figure 2A:
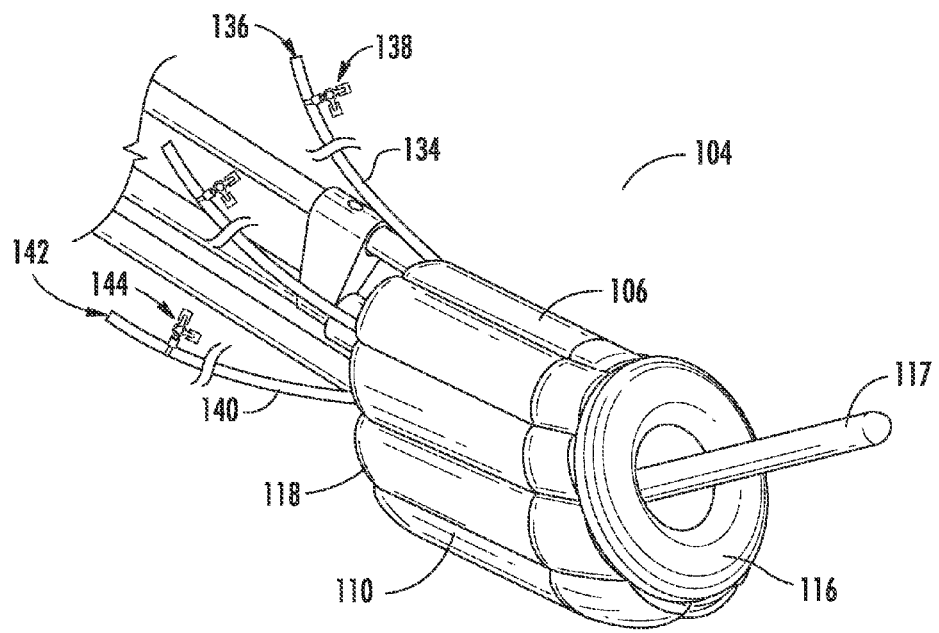
FIG. 2A is a schematic illustration of an example multi-segmented inflatable sleeve positioned on an example applicator for use in brachytherapy treatment.
Figure 2B:
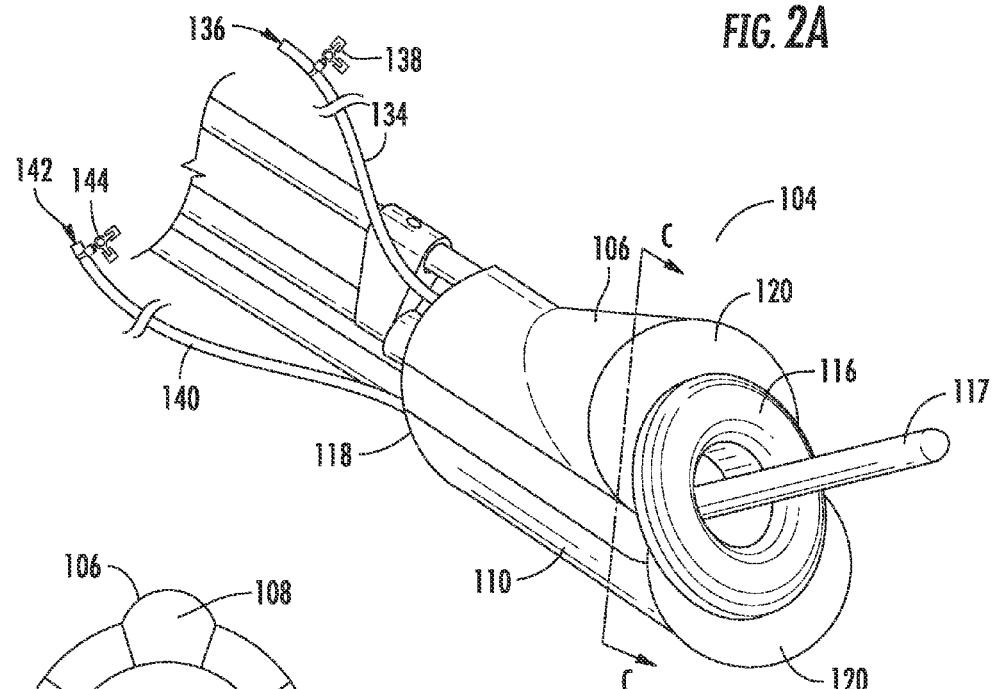
FIG. 2B is a schematic illustration of an example multi-segmented inflatable sleeve positioned on an example applicator and having a plurality of inflated segments for use in brachytherapy treatment.
Figure 2C:
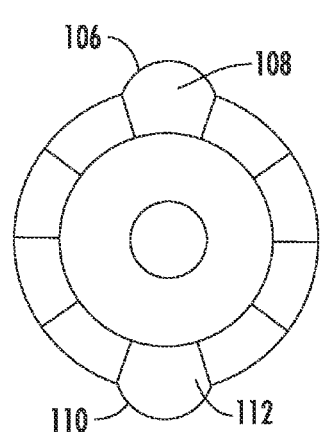
FIG. 2C is a schematic illustration of the cross-section across line C-C of FIG. 2B.

FIGS. 1-2 show an example multi-segmented inflatable device. The device comprises a sleeve 102. The sleeve 102 comprises a first inflatable segment 106 having a primary lumen 108 and a second inflatable segment 110 having a primary lumen 112. The sleeve 102 can optionally define a central passage 114 configured for positioning over the applicator 104. For example, the applicator 104 can comprise a shaft portion over which the sleeve 102 can be placed. The sleeve 102 can also be secured or attached to the applicator 104, for example, with the use of a clip or other securing device.

The first 106 and second 110 segments, and other segments of the sleeve, are selectively inflatable by delivery of fluid into each lumen (108 and 112). Since they are selectively inflatable, the segments can optionally be independently inflated and deflated relative to each other. As used herein, a fluid means a flowable composition. Example fluids include liquids, gases and combinations thereof. For example, a liquid fluid may be water or a contrast agent solution. An example gas is air. For example, with a vaginal applicator, the volume of liquids, gases, or a combination thereof, in the inflatable segment is optionally between 25 cc and 50 cc.

Optionally the sleeve 102 comprises more than two inflatable segments. For example, the sleeve can comprise at least one additional inflatable segment 132 having a primary lumen. As with the first two inflatable segments, each additional inflatable segment is selectively inflatable by delivery of fluid into the lumen. Segments of the sleeve can be selectively inflated to move subject tissue away from a radiation source. It can be determined where a radiation source will be positioned relative to patient tissue and a segment can then be inflated that moves tissue away from the radiation source thereby reducing or eliminated the amount of radiation delivered by the radiation source to the moved tissue.

Optionally, a tube 134 communicates with the inflatable segment 106 such that liquids, gases, or a combination thereof are deliverable to inflatable segment 106 through the tube. For example, tube 134 comprises a proximal end and distal end, wherein the distal end is optionally attached to inflatable segment 106. The proximal end 136 of tube 134 can optionally be used to inject or insert liquids, gases, or a combination thereof into tube 134. A stop cock 138 may optionally be used to hinder, prevent, or allow gases, liquids, or a combination thereof to flow through tube 134.

A tube and stop cock may optionally be attached to each inflatable segment. For example, FIG. 1A shows an example tube 140 with proximal end 142 and stop cock 144 attached to inflatable segment 110. A syringe may be attached to the proximal end of the tube, wherein liquids, gases, or a combination thereof may be delivered into the tube. Optionally, the stop cock may be engaged to inhibit or allow the flow of liquids, gases, or a combination thereof across the stop cock. For example, once a medical professional has achieved the desired volume of liquids, gases, or a combination thereof in a respective inflatable segment, the stop cock can be engaged to the closed position to prevent any liquids, gases, or a combination thereof from escaping from inflatable segment. This maintains the segment at a desired level of inflation. Optionally, at the conclusion of a medical procedure, the stop cock can be disengaged to allow the liquids, gases, or a combination thereof to exit the inflatable segment and flow past the stop cock and out of the tube, resulting in deflation of a given segment.

There are many different commercial embodiments of applicators used by medical professionals and the medical community for brachytherapy procedures for the treatment of cancer. The described sleeve can be used with any of these applicators. Current applicator embodiments include, for example, a ring applicator, a vaginal cylinder, a tandem and ovoid applicator, and an endorectal applicator. Optionally, the described sleeves can be provided in various sizes and/or shapes to fit over a variety of applicators. For example, the sleeve may be optionally designed to inflate in a shape or to a size that is directly related to the movement of specific human tissue, organs, or other critical normal systems. Optionally, the shape and size of the sleeve varies depending on the location in the human body of a specific procedure and which organ(s), tissue, or other critical normal systems may need to be repositioned or moved, to allow the medical professional to move sources closer to a tumor.

When fluid is delivered into the primary lumen of a segment, the segment inflates to assume an expanded inflated shape. The inflated shape moves tissue away from the brachytherapy applicator 104 and, during treatment of the subject, away from sources of radiation used for treatment of the subject.

Methods of treating a cancerous, precancerous or proliferative condition using the sleeve 102 include positioning a brachytherapy applicator 104 into a cavity of a subject, wherein the sleeve of is positioned about the applicator. One or more of the segments (e.g. 106 and 110) are inflated within the cavity by administering fluid into the primary lumen of each inflatable segment. Inflating one or more segments (e.g. 106 and 110) causes movement of tissue away from the brachytherapy applicator 104. In this way, radiation exposure to the moved tissue is reduced or eliminated.

In addition to a shaft portion, the applicator optionally comprises a distal ring 116. The sleeve 104 has a proximal 118 and distal end 120 and, during treatment procedures, the distal end 120 is configured for positioning proximate to the distal ring 116 of the applicator 104.

Figure 4:
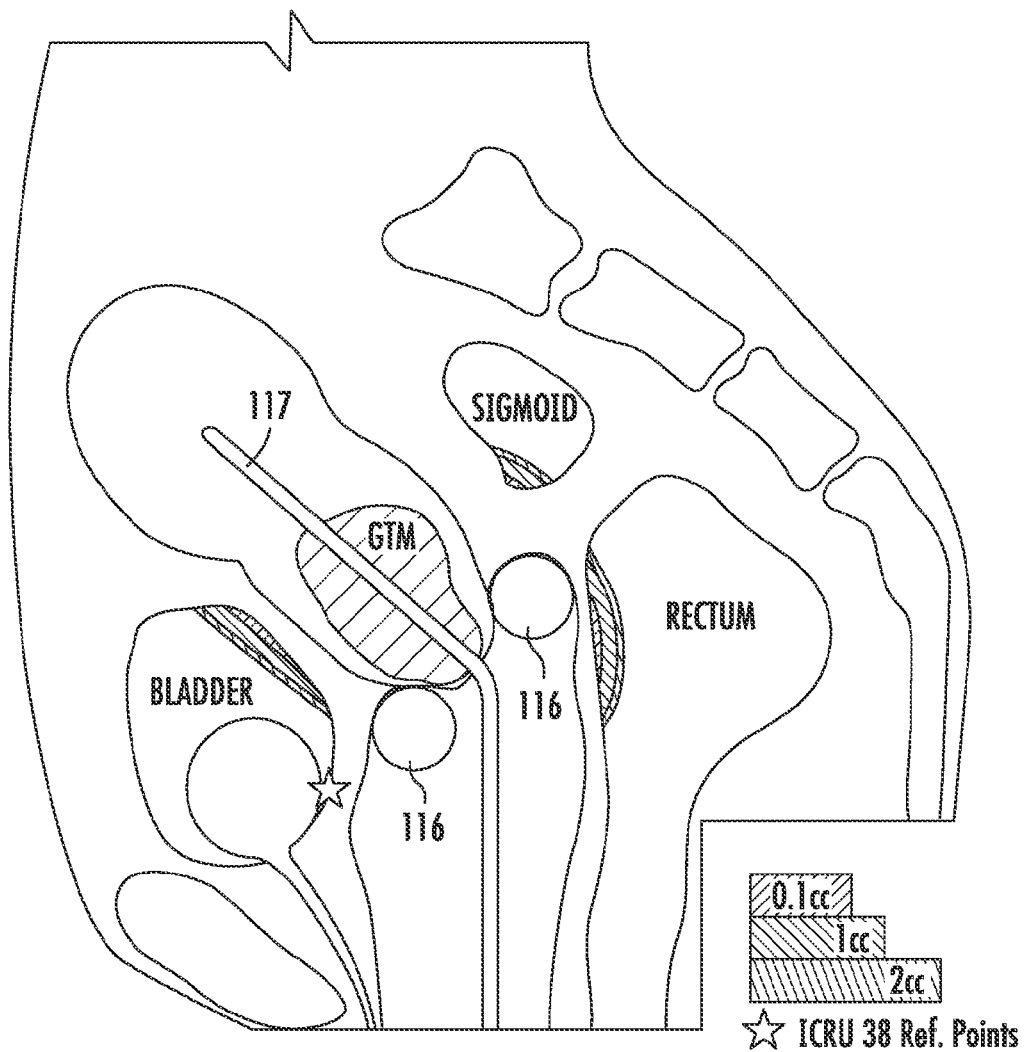
FIG. 4 is a schematic cross-sectional illustration of an applicator positioned in the vagina and uterus of a subject for gynecological brachytherapy treatment.

When treating gynecological cancer, the applicator 104 can be advanced in the subject's vagina until the ring 116 is positioned just distal to the cervix. Example positioning is shown in FIG. 4. The sleeve 102 is optionally positioned on the applicator 104 just distal to the ring 116. From this sleeve position, distal to the ring and distal, bat proximate to the cervix, the inflated segments can move at risk tissue away from a radiation source during brachytherapy treatment procedures.

Figure 3A:
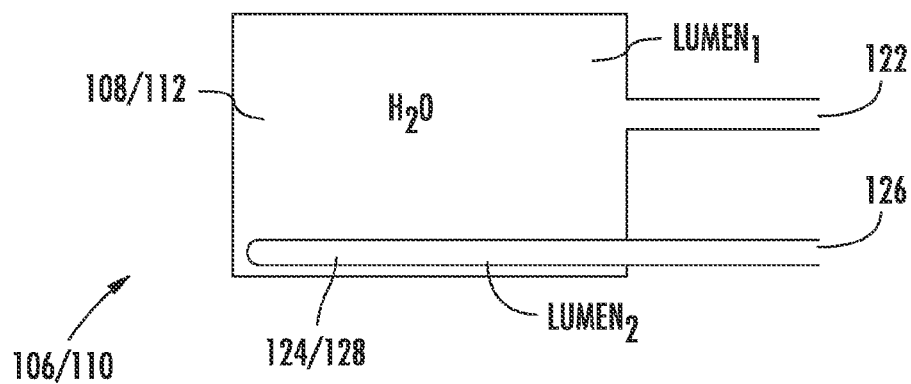
FIG. 3A is a cross-sectional schematic illustration of a segment of an example multi-segmented inflatable sleeve wherein the segment comprises two lumens.

As shown in FIG. 3, each inflatable segment (e.g. 106, 110 and 132) of the sleeve can optionally comprise one or more lumen (e.g. 124) in addition to that segment's primary lumen. For example, the first inflatable segment 106 can comprise a second lumen 124 located at least partially within the primary lumen 108 of the first segment 106. The second inflatable segment 110 can also comprise a second lumen located at least partially within the primary lumen of the second segment. Any additional inflatable segment can comprise a second lumen located at least partially within the primary lumen of that additional segment. Each segment can also comprise more than two lumens.

Each lumen of an inflatable segment is configured to receive fluid so that it can be inflated. In this regard, the sleeve 102 optionally comprises at least one conduit in fluid communication with the primary and second lumen of each segment. For example, in regard to the segment 106, a conduit 122 is in communication with the primary lumen 108, and a conduit 126 is in communication with the second lumen 124.

Figure 3B:
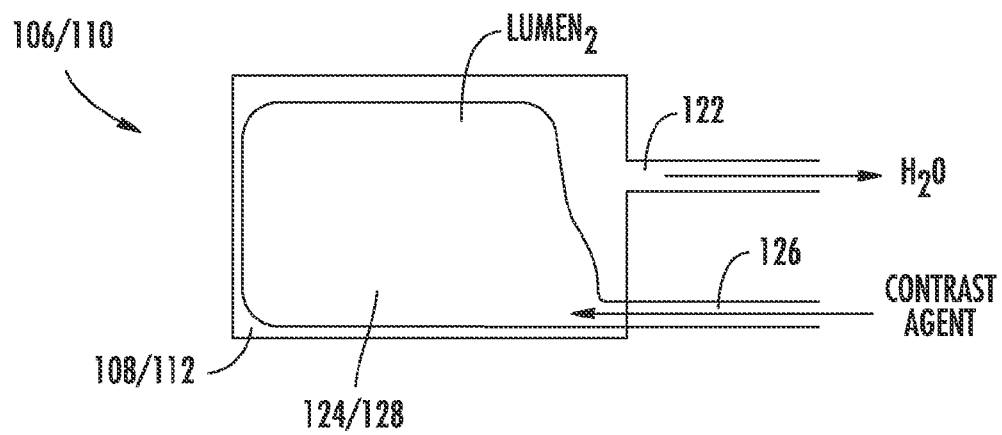
FIG. 3B is a cross-sectional schematic illustration of a segment of an example multi-segmented inflatable sleeve wherein the segment comprises two lumens.

As shown in FIG. 3B, the conduits are optionally used not only to receive fluid into a given lumen, but also to act as an exit port for fluid leaving a lumen. Optionally, each lumen is in fluid communication with a delivery conduit and a removal conduit.

One or more lumens of a given segment are optionally located wholly or partially within another lumen of that segment. When two or more lumens are superimposed in this manner, the segment can first be inflated by administering fluid to an outside lumen (e.g. the primary lumen 108) that houses an additional lumen (e.g. the second lumen 124).

The volume of fluid delivered to the outside lumen can inflate the segment causing movement of tissue. Fluid can then be added to the interior lumen causing it to inflate. As the interior lumen fills with fluid it enlarges to fill a portion or all of the inner-luminal space of the outer lumen. Thus, when fluid is added to the inner lumen, a corresponding volume of fluid can be removed or allowed to flow out of the outer lumen.

While fluid is added to the inner lumen the inflated shape of the segment can be substantially maintained. For example, the shape can be substantially maintained upon administration of fluid to the second lumen 124 of the first segment 106 and removal of the corresponding fluid volume from the primary lumen 108 of the first segment 106.

Further provided are systems for providing brachytherapy treatment. An example system comprises a brachytherapy applicator 104 for insertion into a cavity of a subject. The cavity is optionally selected from the group consisting of a vagina, anus, rectum, esophagus, gastro-intestinal track, and a vessel. The sleeves described herein can be positioned on the applicator prior to insertion of the applicator and sleeve into the cavity.

The system further comprises a sleeve 102 for positioning and securing about the brachytherapy applicator 104. Example sleeves are described above and may optionally comprise a first inflatable 106 segment having primary lumen 108 and a second inflatable segment 110 having a primary lumen 112.

The first 106 and second 110 segments are selectively inflatable by selective delivery of fluid into each primary lumen (108 and 112). The system further comprise a fluid delivery apparatus for delivering fluid into each primary lumen, wherein the fluid delivery apparatus delivers the fluid with sufficient force to cause inflation of each segment and movement of subject tissue when said applicator and sleeve are positioned within the cavity. The sufficient force includes providing a large enough pressure, for example, by forceable delivery of fluid into at least one segment, to inflate the segment to cause movement of subject tissue away from the radiation source.

The sleeves and systems can be used in methods of treating a subject using brachytherapy. For example, an applicator 104 and sleeve 102 can be positioned in a cavity of a subject. The cavity is optionally selected from the group consisting of vagina, anus, rectum, esophagus, gastro-intestinal track, and a vessel.

While the sleeve 102 is in the subject's cavity, fluid is administered to the primary lumen of at least one or a plurality of segments. For example, water can be administered into a primary lumen to inflate a segment. After inflation of the segment by administering fluid to the primary lumen, an image is taken of the subject to visualize a treatment field of the subject. For example, a computed tomographic image or a magnetic resonance image can be taken to plan for brachytherapy treatment radiation exposure profiles.

Optionally, a contrast agent solution can then be administered to one or more second lumen positioned within a primary lumen or to another inner lumen, while allowing a volume of water corresponding to the volume of administered contrast agent solution to be removed from each primary lumen or outer lumen. Once contrast agent has been used to inflate a segment by filling the second or inner lumen, radiation is applied to the subject wherein the inflatable segments reduce radiation delivered to the tissue of the subject moved away from the brachytherapy applicator.

An example method includes moving tissue or a selected portion of tissue by filling the corresponding inflatable segment or segments with liquids, gases, or a combination thereof. After selection of a cavity, the corresponding inflatable segment or segment can be optionally inflated or filled to move away surrounding tissue or selection of tissue.

Also provided is a method of reducing radiation exposure of tissue in a subject that comprises inflating an inflatable device with a contrast agent wherein the inflating expands the size of the device and causes movement of the tissue. The method further comprises applying radiation to the subject, wherein exposure of the moved tissue is reduced (e.g. eliminated).

For example, the provided methods and systems of the present invention can optionally be used to treat endometrial, cervical, anal, or rectal cancerous, precancerous, or proliferative conditions. Especially in cases in which several treatments are necessary to treat the cancerous, precancerous, or proliferative condition, the systems and methods optionally allow for the medical professional to simulate a prior treatment by refilling the applicable inflatable segment (s) with the same volume of liquids, gases, or a combination thereof, as used in the previous treatment or medical procedure.

EXAMPLES

High dose rate (HDR) brachytherapy is art effective treatment modality to treat cancer of the uterine cervix. Reducing doses to the rectum and bladder potentially reduces late complications. Conventionally, various approaches including gauze packing, rectal retraction, posterior vaginal speculum blade, and/or an inflatable catheter bulb have been recommended to displace organs at risk (OARs) and increase the therapeutic ratio. Vaginal balloon packing (VBP) is described to displace OARs during HDR treatment of the uterine cervix.

Figure 5:
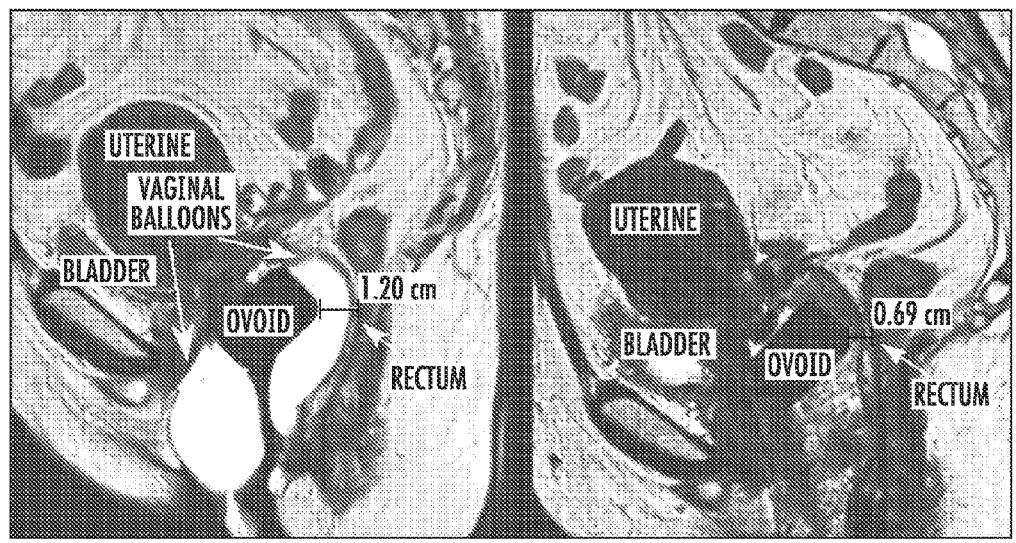
FIG. 5 are magnetic resonance images of vaginal balloons in treatment position compared with use of conventional radiopaque gauze for same patient. The off-center rectum displacement from the ovoid tip is larger when vaginal balloon packing (VBP) is used (left panel) compared with that when radiopaque gauze is used (right panel). The vaginal balloons were filled with saline solution in this case.

FIG. 5 shows an example of the use of VBP in an HDR treatment using a tandem-and-ovoid applicator compared with conventional gauze packing. The advantages of using a VBP approach include larger OAR displacement and better reproducibility. Herein, it is shown that VBP reduces the radiation dose to the bladder and rectum by increasing the distance from the source coupled with additional shielding when filled with contrast agents.

The vaginal balloon (RadiaDyne, Houston, Tex.) is approximately a semi-sphere in shape when filled with material, air, water, or contrast agent. The contrast agents studied include the Optiray series (Mallinckrodt, Hazelwood, Mo.) of various concentrations and Magnevist and Eovist (Bayer Healthcare Pharmaceuticals, Wayne, N.J.). Iodine is the effective element in Optiray products, whereas gadolinium is the effective element in Magnevist and Eovist.

The K-shell electron binding energy is 33 keV for iodine and 50 keV for gadolinium. Both elements have high attenuation coefficients due to photoelectric effect for kV x-rays or g-rays of kiloelectron volt energy level. The enhanced photon absorption in the solution is due to the large number of the photoelectric events because of the presence of iodine or gadolinium.

The active radiopaque ingredient in Optiray320 is 678 mg/mL, of ioversol ($C_{18}H_{24}I_3N_3O_9$; molecular weight, 807.2 g). The quantity of iodine in Optiray320 solution is 320 mg/mL. The density of Optiray in human body temperature (37 C) is 1.371 g/mL. The iodine concentration in Optiray is 23.3% by weight. Optiray350 was also used, which has 350 mg/mL of iodine (24.9% by weight), the highest concentration in the Optiray series, and Optiray160, which has 160 mg/mL of iodine (13.5% by weight), the lowest concentration in the series. The densities of these two agents are 1.405 and 1.188 g/mL, respectively, at body temperature.

Optiray products of other iodine concentrations are also simulated with Monte Carlo

TABLE 1

| Contrast Agent | Density (g/mL) | I | Gd | C | O | H | N | Na |
|---|---|---|---|---|---|---|---|---|
| Optiray160 | 1.188 | 0.1347 | 0 | 0.0776 | 0.6846 | 0.0878 | 0.0152 | 0 |
| Optiray240 | 1.281 | 0.1874 | 0 | 0.1074 | 0.6054 | 0.0787 | 0.0210 | 0 |
| Optiray300 | 1.352 | 0.2219 | 0 | 0.1269 | 0.5535 | 0.0728 | 0.0248 | 0 |
| Optiray320 | 1.371 | 0.2335 | 0 | 0.1334 | 0.5362 | 0.0708 | 0.0260 | 0 |
| Optiray350 | 1.405 | 0.2492 | 0 | 0.1423 | 0.5126 | 0.0681 | 0.0278 | 0 |
| Magnevist | 1.195 | 0 | 0.0657 | 0.1411 | 0.6736 | 0.0901 | 0.0294 | 0 |
| Eovist | 1.088 | 0 | 0.0361 | 0.0634 | 0.7812 | 0.0990 | 0.0097 | 0.0106 |

The Magnevist solution contains 469 mg/mL of gadopentetate dimeglumine ($C_{28}H_{54}GdN_5O_{20}$; molecular weight, 938 g). The concentration of the effective element, gadolinium, is 6.6% by weight in Magnevist. The density at normal body temperature is 1.195 Ont. The effective component in Eovist is gadoxetate disodium ($GdC_{23}H_{28}N_3O_{11}Na_2$; molecular weight, 725.7 g). The concentration of gadoxetate disodium Eovist is 181.4 mg/L. The corresponding gadolinium concentration in Eovist is 3.6% by weight. At normal body temperature, the density of the solution is 1.088 g/mL. The contrast agents studied are listed in Table 1. Complete chemical composition data of the agents (Table 1) were used in the cross-sectional data generation for the MC simulations in this description.

Figure 6A:
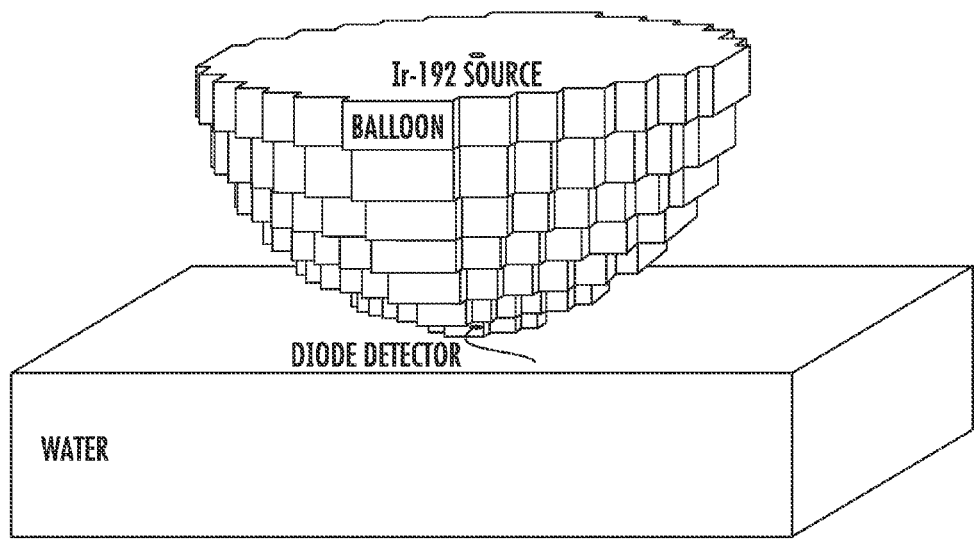
FIG. 6A is a measurement and Monte Carlo simulation setup for dose reduction comparison.

The HDR delivery system used was a Nucletron microSelectron HDR unit (Nucletron, Veenendaal, The Netherlands). The vaginal packing balloon was filled with 50 mL of air, saline solution, and Optiray320 (contrast) for each measurement. The diode detector used in the measurements was a Scanditronix EDP 23 G p-type detector (Scanditronix Medical AB, Uppsala, Sweden). It has buildup of 0.5 mm (or 0.2 g/cm2) of epoxy. It was placed on the balloon with a 3-mm bolus between the detector and the balloon. The Ir-192 source was electronically placed at the other end of the balloon (FIG. 6A). For each balloon-filling material, three consecutive measurements of a 60-second irradiation were performed. The ratios of contrast to saline solution and contrast to air were determined by use of mean readings of each material. A computed tomography (CT) scan was performed for each type of material in the balloon to ensure that the diameter difference was within 1 mm for all three types of measurements.

An EGSnrc-based MC simulation program, DOSXYZnrc, was used. The cross-sectional data of the contrast agents were generated by use of PEGS in EGSnrc based on the chemical composition. The saline solution in the measurement setup was approximated with water in simulations. The Ir-192 radiation source was approximated with a point source. All the simulations used the energy spectrum of the Ir-192 source. Two different setups were simulated (FIG. 6).

The first one was to compare with measurements; thus the balloon was surrounded by air (A). In the second setup, the balloon was surrounded by water instead (B). The semi-sphere balloon is approximated by seven circular discs of uneven thicknesses and radii, and the circular discs are also approximated by multi-step polygons. The semicircular shape in simulations is a 28-sided polygon from a side view. These approximations make simulations of such geometry by use of DOSXYZnrc possible.

Figure 6B:
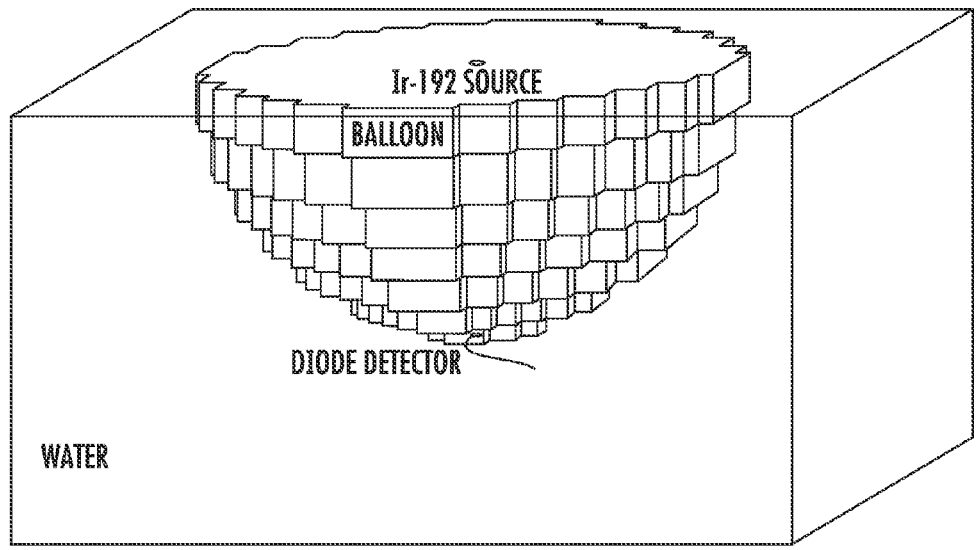
FIG. 6B is a Monte Carlo simulation setup for dosimetric evaluation.

The balloon in FIG. 6 was filled with air, water, Optiray of different iodine concentrations, Magnevist, or Eovist, respectively, in the simulations. Each simulation took about 30 hours of central processing unit (CPU) time on a Linux platform of a 3-GHz CPU, with the number of histories between 3.5 and 4 billion. With this setup, the standard deviation of the calculated dose in a step size of 0.5 mm along the central axis of the balloon was lower than 2% for all cases. With the setup shown in FIG. 6B, various radii of the semi-sphere balloons were simulated for a further dosimetric study.

Calculation-measurement comparison with the semi-sphere balloon radius at 3.4 cm, the measured mean ratio +/−1 SD was 0.922+/−0.002 for Optiray320/saline solution and 0.808+/−0.001 for Optiray320 air, with a 3-mm bolus between the balloon and the diode dosimeter. The MC-calculated ratios using a semi-sphere setup (FIG. 6A) were 0.895+/−0.010 for Optiray320/water and 0.781+/−0.010 for Optiray320/air.

Figure 7A:
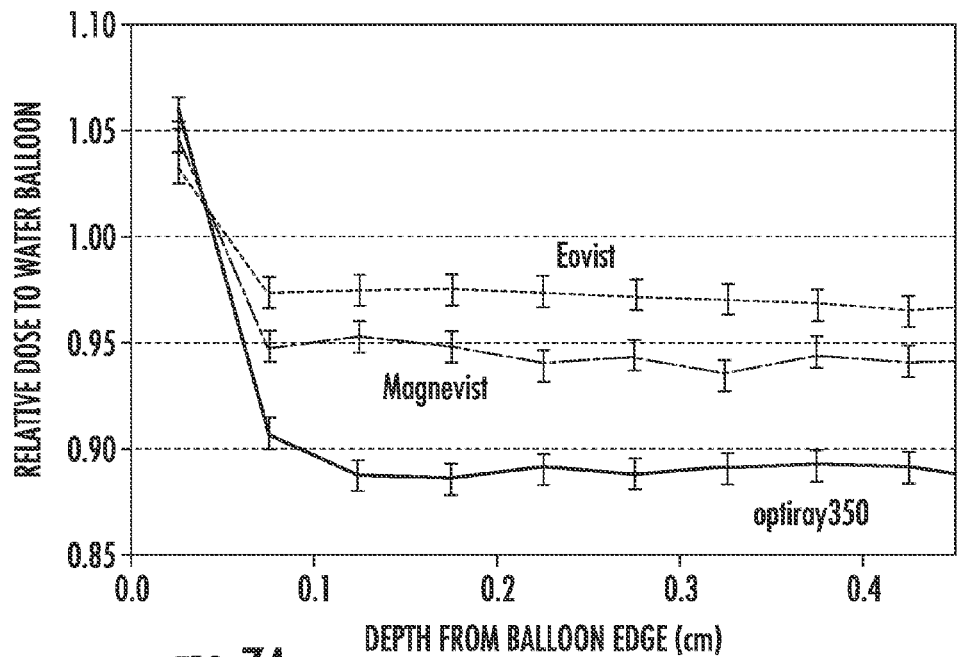
FIG. 7A is a Monte Carlo calculated dose ratio graph. Dose ratios of contrast/water were determined along the central axis after use of semi-sphere balloon of 3.0 cm in radius. The dose ratios at the first point after the balloon edge are greater than unity, indicating higher doses than those if the balloon is filled with water instead. The ratios drop to flat values around 1 mm from the balloon edge.
Figure 7B:
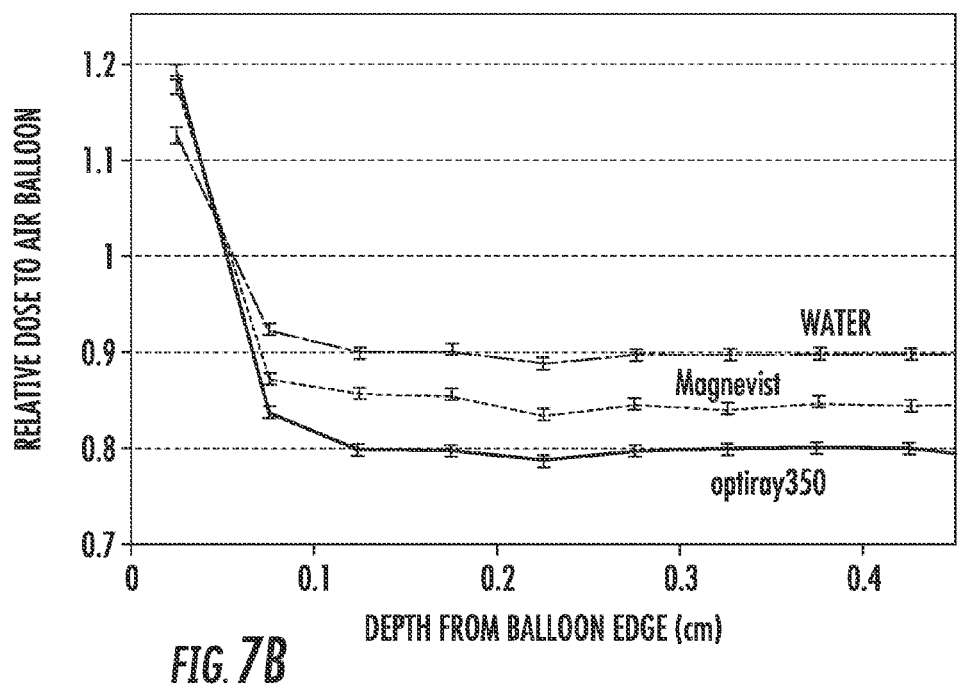
FIG. 7B is a Monte Carlo calculated dose ratio graph. Dose ratios of water or contrast to air were determined along the central axis after use of a semi-sphere balloon of 3.0 cm in radius. The water/air dose ratios close to the balloon edge are an example of the build-down effect, which is introduced by the density difference. The other contrast to water or to air dose ratios are results of the enhanced build-down effect due to additional photoelectrons generated inside the contrast-filled balloon.

The dose reduction in MC calculations was slightly more significant than measurements build-down effect. In addition to good agreement between the measurement and calculation, the MC simulations showed that the dose just outside the contrast-filled balloon is even higher than that of a water-filled balloon. The dose drops of to be lower than that of a water-filled balloon in a short range. FIG. 7A shows an example of 3.0 cm of balloon radius. In this example the fall-off range is about 1 mm (third point from balloon edge). After this range, the dose ratio of Optiray350/water is flat vs. depth at about 88.6%. The dose reduction is thus 11.4% compared with the water-filled balloon. This phenomenon is explained by the commonly referred to "build-down" effect. When photon radiation traverses across high-low density interface from high density to low, the dose on the low density side close to the interface is usually higher than that if the high density volume is replaced by the same low density material, if the high density volume is not great. This is because in the high density volume, more electrons are set into motion by the photons. At the border, more electrons thus enter the low-density volume, introducing higher dose in a short range. This concept of build-down effect, which is caused by density difference, is illustrated by the relative dose curve of water balloon vs. air balloon in FIG. 7B.

Besides the contribution of the higher density of the contrast agents inside the balloon, this build-down effect is further enhanced by the photoelectric effect. A large number of photoelectric events occur inside the contrast-filled balloon because of the presence of the contrast agent. The product of a photoelectric event is an electron ejected from the involved iodine/gadolinium atom. When this event happens close to the edge of the balloon, the electron can travel across the edge before being absorbed. The photoelectrons that cross the boundary, in relatively large numbers, also contribute to the relatively high dose just outside the balloon. The range of the photoelectrons is usually short, and it does not change with balloon size. Thus this "dose boost" region is short.

For a balloon radius range between 1.4 and 3.8 cm, dose ratios of contrast/water, contrast/air, and water/air are higher than unity at 0.25 mm outside the balloon, but flat ratios lower than unity are reached around 1 mm outside the balloon (FIG. 7).

Figure 8A:
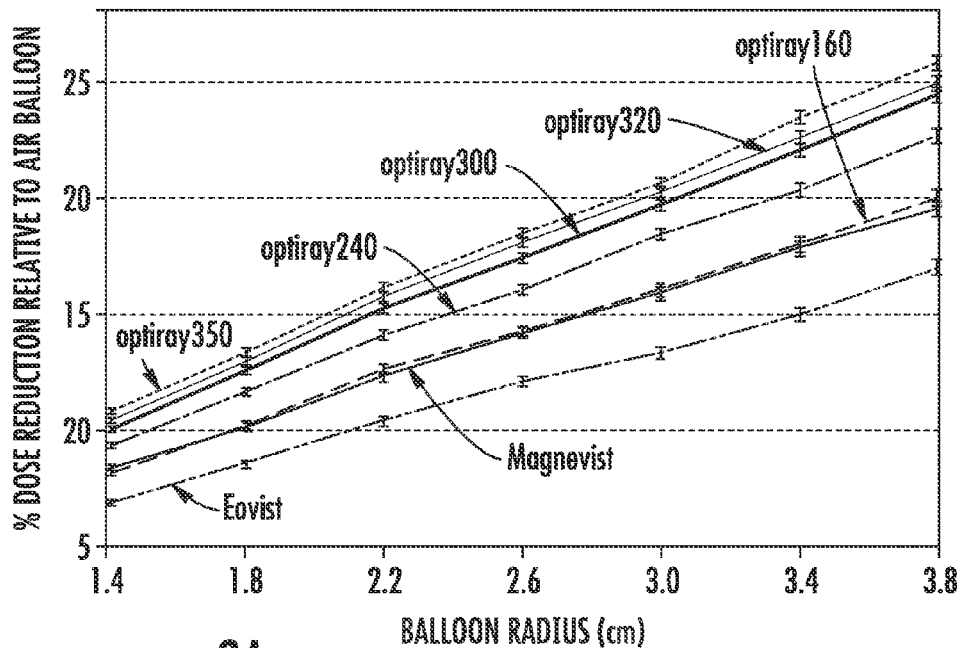
FIG. 8A is a graph showing data from Monte Carlo calculated dose reduction vs. balloon size and balloon filling in reference to an air balloon.
Figure 8B:
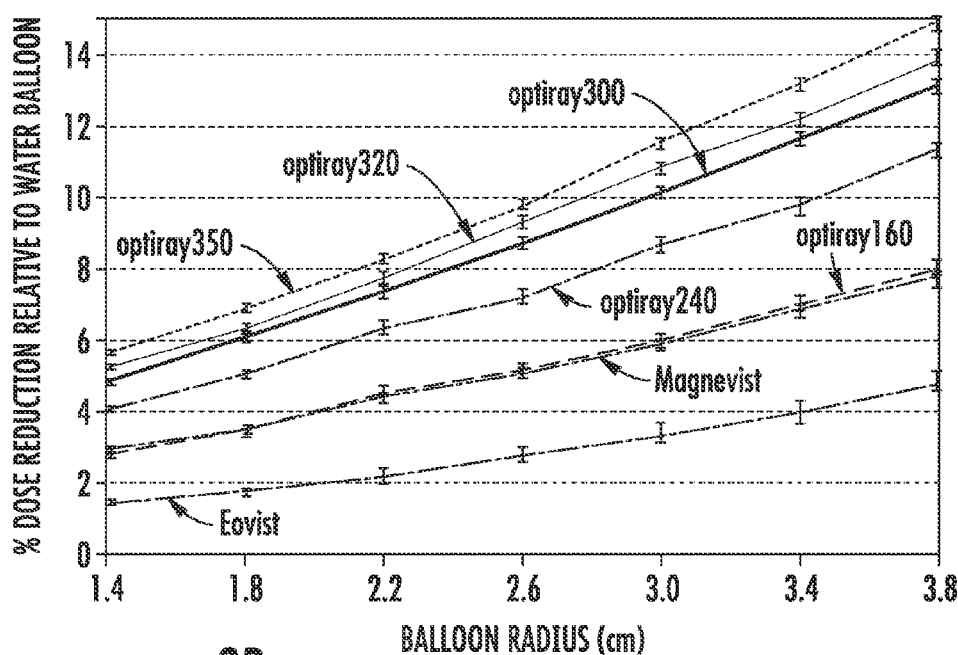
FIG. 8B is a graph showing data from Monte Carlo calculated dose reduction vs. balloon size and balloon filling in reference to a water balloon.

FIG. 8 illustrates the relative dose reduction vs. balloon size for different contrast materials. As expected, the larger contrast-filled balloon provides higher dose reduction because of increased attenuation to the g-rays due to the photoelectric effect. At the balloon size range of 1.4 to 3.8 cm in radius, the dose reduction of an Optiray350-filled balloon is in the range of 5.5% to 14.8% compared with that of the water-fitted balloon and 10.7% to 25.8% compared with that of the air-filled balloon.

For all the contrast agents used, the dose reduction along the central axis of the balloon is approximately linear to the balloon size; thus the dose reduction of an arbitrary size can be predicted by use of the corresponding fitted linear equation.

Although gadolinium has a higher atomic number and Kshell electron binding energy and thus higher photoelectric cross section for kiloelectron volt g-rays, due to the much lower gadolinium concentration in Magnevist and Eovist (7% and 4%, respectively, by weight) compared with the iodine concentration in the Optiray series (13-25%), as well as lower density (Table 1), the dose reduction of the two gadolinium-based agents is less than that of the Optiray series, whereas the dose reduction values were close to each other for Magnevist and Optiray160 (FIG. 8).

Because these gadolinium-based agents are more expensive than Optiray, Optiray is also a better option economically. The relative dose reduction is approximately linearly proportional to the concentration of iodine in the contrast solution. Thus a linear equation can be used to predict the relative dose reduction of an arbitrary concentration of a certain type of contrast solution.

Dose reduction was achieved by using a contrast-filled VBP system in HDR brachytherapy of the uterine cervix. This approach not only provides an increase the distance from source but can also provide shielding when filled with contrast agents. The dose reduction values presented in this example are based on contributions from replacing the balloon filling with contrast material. The inverse square law applies in this respect no matter whether the balloon is filled with air, water, or contrast material. In addition to the larger distance from the radiation source, a larger balloon filled with contrast material further introduces greater attenuation to the photons, thus further reducing radiation dose to OAR. When a contrast-filled balloon is used in HDR treatment, the vaginal wall dose just outside the balloon is higher than that of a water-filled balloon. Optionally, to eliminate the increased dose to the vaginal wall the balloon wall has about a 1 mm thickness to absorb the excess photoelectrons. However, doses in the more radiosensitive organs, such as the bladder and rectum, which are further away from the balloon, are reduced even if the balloon is thinner than 1 mm. The contrast filling in VBP does not introduce any artifact to magnetic resonance imaging (MRI). The dose reduction method is thus a good fit to MRI-based planning. If treatment planning is CT-based, the artifact introduced by the high concentration contrast optionally obscures the source localization markers and relevant anatomy. To avoid this, saline solution may be used when the CT simulation is taken, and contrast of the same volume replaces saline solution before treatment.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A sleeve for positioning on a brachytherapy applicator, comprising:
   (a) a first inflatable segment having an expandable primary lumen and a second lumen located at least partially within the primary lumen of the first inflatable segment;
   (b) a second inflatable segment having an expandable primary lumen and a second lumen located at least partially within the primary lumen of the second inflatable segment; and
   (c) a central passage configured for positioning over the brachytherapy applicator; wherein the first and second segments are selectively inflatable by delivery of fluid into each lumen, and further wherein the first and second segments are equidistant from a longitudinal axis of the central passage, and the first and second segments are in a same latitudinal plane in relation to the longitudinal axis; and
   wherein the primary lumen of either the first or second segment is inflatable independent of the second lumen of the same segment, wherein inflation of the second lumen of either the first or second segment causes deflation of the primary lumen of the same segment by a corresponding volume such that a total volume of fluid in the segment stays the same.

2. The sleeve of claim 1, wherein the sleeve has a proximal and distal end and wherein the distal end is configured for positioning proximal to a distal ring of the brachytherapy applicator.

3. The sleeve of claim 1, further comprising at least one conduit configured for delivering fluid into the primary lumen of the first inflatable segment.

4. The sleeve of claim 3, further comprising at least one conduit configured for delivering fluid into the primary lumen of the second inflatable segment.

5. The sleeve of claim 4, further comprising at least one conduit configured for delivering fluid into the second lumen of the second inflatable segment.

6. The sleeve of claim 5, wherein each inflatable segment comprises more than two lumens.

7. The sleeve of claim 5, wherein the fluid delivered into the first or second lumen of each inflatable segment is a contrast agent.

8. The sleeve of claim 5, further comprising at least one conduit for removal of fluid from the primary or second lumen of the first segment and at least one conduit for removal of fluid from the primary or second lumen of the second segment.

9. The sleeve of claim 3, further comprising at least one conduit configured for delivering fluid into the second lumen of the first inflatable segment.

10. The sleeve of claim 9, wherein the fluid delivered into the first or second lumen of the first inflatable segment is a contrast agent.

11. The sleeve of claim 1, further comprising a securing member for securing the sleeve to the brachytherapy applicator.

12. The sleeve of claim 1, further comprising at least one additional inflatable segment having a primary lumen, wherein the at least one additional inflatable segment is selectively inflatable by delivery of fluid into the primary lumen.

13. The sleeve of claim 1, wherein each inflatable segment is configured to assume an inflated shape from fluid delivered into the primary lumen of each respective segment.

14. The sleeve of claim 1, wherein the first inflatable segment is inflatable with liquids, gases, or a combination thereof.

15. The sleeve of claim 1, wherein the second inflatable segment is inflatable with liquids, gases, or a combination thereof.

16. A system for providing brachytherapy treatment, comprising:
   (a) a brachytherapy applicator for insertion into a cavity of a subject;
   (b) a sleeve for positioning about the brachytherapy applicator, said sleeve comprising a first inflatable segment having an expandable primary lumen and a second lumen located at least partially within the primary lumen of the first inflatable segment; and a second inflatable segment having an expandable primary lumen and a second lumen located at least partially within the primary lumen of the second inflatable segment; a central passage configured for positioning over the brachytherapy applicator; wherein the first and second inflatable segments are selectively inflatable by delivery of fluid into each lumen, and further wherein the first and second segments are equidistant from a longitudinal axis of the central passage, and the first and second segments are in a same latitudinal plane in relation to the longitudinal axis; and wherein the primary lumen of either the first or second segment is inflatable independent of the second lumen of the same segment, wherein inflation of the second lumen of either the first or second segment causes deflation of the primary lumen of the same segment by a corresponding volume such that a total volume of fluid in the segment stays the same; and
   (c) a fluid delivery apparatus for delivering fluid into each primary lumen, wherein the fluid delivery apparatus delivers the fluid with sufficient force to cause inflation of each segment and movement of subject tissue when said applicator and sleeve are positioned within the cavity.

17. The system of claim 16, wherein the cavity is selected from the group consisting of a vagina, anus, rectum, esophagus, gastro-intestinal tract, and a vessel.

18. A method of treating a cancerous, precancerous or proliferative condition, comprising:
   (a) positioning a brachytherapy applicator into a cavity of a subject, wherein the sleeve of claim 1 is positioned about the applicator; and
   (b) inflating at least one of the first and second inflatable segments by administering fluid into the primary lumen of each inflatable segment to move tissue of the subject away from the brachytherapy applicator.

19. The method of claim 18, wherein the fluid administered is water.

20. The method of claim 18, wherein an image is taken of the subject to visualize a treatment field of the subject.

21. The method of claim 18, further comprising administering a contrast agent solution to each second lumen while allowing a volume of water corresponding to the volume of administered contrast agent solution to be removed from each primary lumen.

22. The method of claim 21, further comprising applying radiation to the subject wherein the inflatable segments reduce radiation delivered to the tissue of the subject moved away from the brachytherapy applicator.

23. The method of claim 21, wherein the cavity is the vagina and wherein the sleeve is positioned proximate to the cervix.

24. The system of claim 16, wherein the cavity is selected from the group consisting of a vagina, anus, rectum, esophagus, gastro-intestinal tract, and a vessel.

25. A method of reducing radiation exposure of tissue in a subject, comprising:
 (a) providing an inflatable device comprising a first inflatable segment having an expandable primary lumen and a second lumen located at least partially within the primary lumen of the first inflatable segment, wherein the inflatable device further comprises a second inflatable segment having an expandable primary lumen and a second lumen located at least partially within the primary lumen of the second segment; wherein the device further comprises a central passage, and wherein the first and second segments are equidistant from a longitudinal axis of the central passage, and further wherein the first and second segments are in a same latitudinal plane in relation to the longitudinal axis;
 (b) inflating at least one of the primary lumen of the first segment and the primary lumen of the second segment with an inflation fluid;
 (c) inflating the second lumen of the same segment as the inflated primary lumen with a volume of contrast agent, wherein inflation of the second lumen causes a corresponding volume of inflation fluid to be removed from the primary lumen; and
 (d) applying radiation to the subject, wherein exposure of the tissue is reduced.

* * * * *